US00PP12027P2

(12) United States Plant Patent
Rother

(10) Patent No.: US PP12,027 P2
(45) Date of Patent: Jul. 31, 2001

(54) SCAEVOLA PLANT NAMED 'WHITE CHAMP'

(76) Inventor: Reinhard W. Rother, 56 Emerald Monbulk Road, Emerald, Victoria 3782 (AU)

( * ) Notice: Subject to any disclaimer, the term of this patent is extended or adjusted under 35 U.S.C. 154(b) by 0 days.

(21) Appl. No.: 09/427,731

(22) Filed: Oct. 27, 1999

(51) Int. Cl.[7] ..... A01H 5/00

(52) U.S. Cl. ..... Plt./363

(58) Field of Search ..... Plt./363

(56) References Cited

PUBLICATIONS

UPOV–ROM GTITM JOUVE Computer Database 2000/04, citation for 'White Champ', Aug. 2000.*

* cited by examiner

*Primary Examiner*—Bruce R. Campell
*Assistant Examiner*—W Couchoud Baker
(74) *Attorney, Agent, or Firm*—C. A. Whealy

(57) ABSTRACT

A distinctive cultivar of Scaevola plant named White Champ, characterized by its low-growing, spreading and cascading growth habit; short internodes; dense and bushy plant form and freely branching plant habit; freely flowering habit with more than 200 flowers and flower buds per plant; and unique large white fan-shaped flowers with yellow green throat.

1 Drawing Sheet

BACKGROUND OF THE INVENTION

The present invention relates to a new and distinct cultivar of Scaevola plant, botanically known as *Scaevola aemula* and referred to by the cultivar name White Champ.

The new cultivar is a product of a planned breeding program conducted by the Inventor in Emerald, Victoria, Australia. The objective of the breeding program was to create new compact Scaevola cultivars.

The new cultivar originated from a cross made by the Inventor in 1996 of two unidentified selections of *Scaevola aemula*. The new Scaevola was selected by the Inventor as a flowering plant within the progeny of this cross in a controlled environment in Emerald, Victoria, Australia.

Plants of the new Scaevola have white flowers whereas plants of the unidentified selections have lavender blue flowers which is typical for the species *Scaevola aemula*. In addition, plants of the new Scaevola have lighter green leaves than plants of the female parent.

Asexual propagation of the new cultivar by terminal cuttings taken in Emerald, Victoria, Australia, has shown that the unique features of this new Scaevola are stable and are reproduced true to type in successive propagations.

SUMMARY OF THE INVENTION

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'White Champ' which distinguish 'White Champ' as a new and distinct cultivar:

1. Low-growing, spreading and cascading growth habit.

2. Short internodes, dense and bushy plant form and freely branching plant habit.

3. Freely flowering, more than 200 flowers and flower buds per plant.

4. Unique large white fan-shaped flowers with yellow green throat.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical hanging basket container with three plants of 'White Champ'.

The photograph at the bottom of the sheet comprises a close-up view of typical flowering stems and leaves of plants of 'White Champ' showing various stages of development and leaf shapes. Flower and foliage colors in the photographs may appear different from the actual colors due to light reflectance.

DETAILED BOTANICAL DESCRIPTION

The following observations, measurements and values describe 20-cm hanging basket containers with three plants each of the new cultivar grown for 8 to 10 weeks during the summer in Bonsall, Calif., under outdoor, full-sun conditions with day temperatures ranging from 21 to 35° C. and night temperatures ranging from 13 to 18° C.

Color references are made to The Royal Horticultural Society Colour Chart except where general terms of ordinary dictionary significance are used.

Botanical classification: *Scaevola aemula* cultivar White Champ.

Parentage:

*Female, or seed, parent.*—Unidentified selection of *Scaevola aemula.*

*Male, or pollen, parent.*—Unidentified selection of *Scaevola aemula.*

Propagation:

*Type cutting.*—Terminal cuttings.

*Time to initiate roots* (*summer*).—About 18 to 25 days at 24° C.

*Time to develop roots* (*summer*).—About 35 days at 24° C.

*Root description.*—Numerous, fine, freely branching.

Plant description:

*Plant form and growth habit.*—Annual container and garden plant. Low-growing, spreading and cascading growth habit. Suitable for hanging basket containers. Numerous leaves and short internodes, full, dense and bushy. Freely branching with about eight lateral branches developing when pinched.

*Crop time.*—About 8 weeks are required to produce a finished, flowering plant in a 12.5-cm container from a rooted cutting.

*Vigor.*—Vigorous.

*Plant height.*—About 18 cm.

*Plant width* (*spread*).—About 47.5 cm.

*Stem description.*—Length: About 46 cm. Diameter: About 3 mm. Internode length: About 2.2 to 3.7 cm. Color: 143A. Texture: Smooth, sparse whitish hairs.

*Foliage description.*—Arrangement: Alternate, single. Quantity per primary lateral stem: About 20. Length: About 3.75 cm. Width: About 2.15 cm. Shape: Spatulate to elliptic with deep serrations; considerably plasticity in leaf shape, gradual size reduction towards lateral branch apex until leaves subtending flowers appear bract-like. Apex: Broadly acute. Base: Cuneate; sessile. Margin: Irregularly serrated. Texture: Very sparsely pubescence on upper suface; tough. Color: Young leaves, upper surface: 144A to 144B. Young leaves, lower surface: 144B. Fully expanded leaves, upper surface: 147B; leaf base, 144B. Fully expanded leaves, lower surface: 146B. Venation, upper and lower surfaces: 144B.

Flower description:

*Flower type and shape.*—Zygomorphic, semi-circular, fan-shaped flowers with five petals fused at the base to form a tubular flower throat. Flower throat open along the upper surface exposing reproductive organs. Flowers persistent. No fragrance detected.

*Flower arrangement and quantity.*—Solitary flowers arise from leaf axils with one flower per axil. Flowers horizontal to perpendicular to stem. Typically about 10 open flowers and about 12 buds per lateral stem; very freely flowering with more than 200 flowers and flower buds per plant.

*Flowering time.*—Plants start flowering when lateral branches are about 10 cm in length; flowers open acropetally. Plants flower continuously from May through October in the Northern Hemisphere. Flowers last about 2 to 3 days on the plant.

*Flower buds.*—Shape: Tubular. Length: About 1.5 cm. Diameter: About 2 mm. Color: 143D.

*Perianth.*—Aspect: Fan-shaped, flat. Length, fan: About 2.5 cm. Width, fan: About 1.3 cm. Height: About 1.8 cm.

*Petals.*—Quantity: Five, fused at base. Shape: Elliptic. Apex: Broadly acute. Margin: Entire. Length, above tube: About 1.2 cm. Width, above tube: About 4 mm. Length, tube: About 1.5 cm. Diameter, tube: About 4 mm. Texture: Smooth. Flower throat, whiskered. Color: When opening, upper surface: 155D; throat, yellow green, 145A. When opening, lower surface and tube: 155D with yellow green longitudinal stripes, 145B. Fully opened, upper surface: 155D; throat, yellow green, 145A and 154A. Fully opened, lower surface and tube: 155D with yellow green stripes, 145B.

*Sepals.*—Quantity and arrangement: Two; opposite. Shape: Narrow, strap-like. Apex: Acute. Margin: Entire. Calyx length: About 1.8 cm. Calyx diameter: About 2.5 mm. Color: Upper surface: 137C. Lower surface: 137D.

*Reproductive organs.*—Androecium: Five stamens. Anthers: Shape: Oblong. Length: About 1.5 mm. Diameter: About 0.5 mm. Color: 165A. Pollen: Very scarce. Pollen color: 165A. Gynoecium: Pistil length: About 1.2 cm. Style length: About 9 mm. Style color: 144D. Stigma shape: Oblong with fine white hairs. Stigma color: 155D. Ovary color: 144C.

Disease resistance: Resistance to pathogens common to Scaevola has not been observed.

Seed production: Seed production has not been observed.

It is claimed:

1. A new and distinct Scaevola plant named White Champ, as illustrated and described.

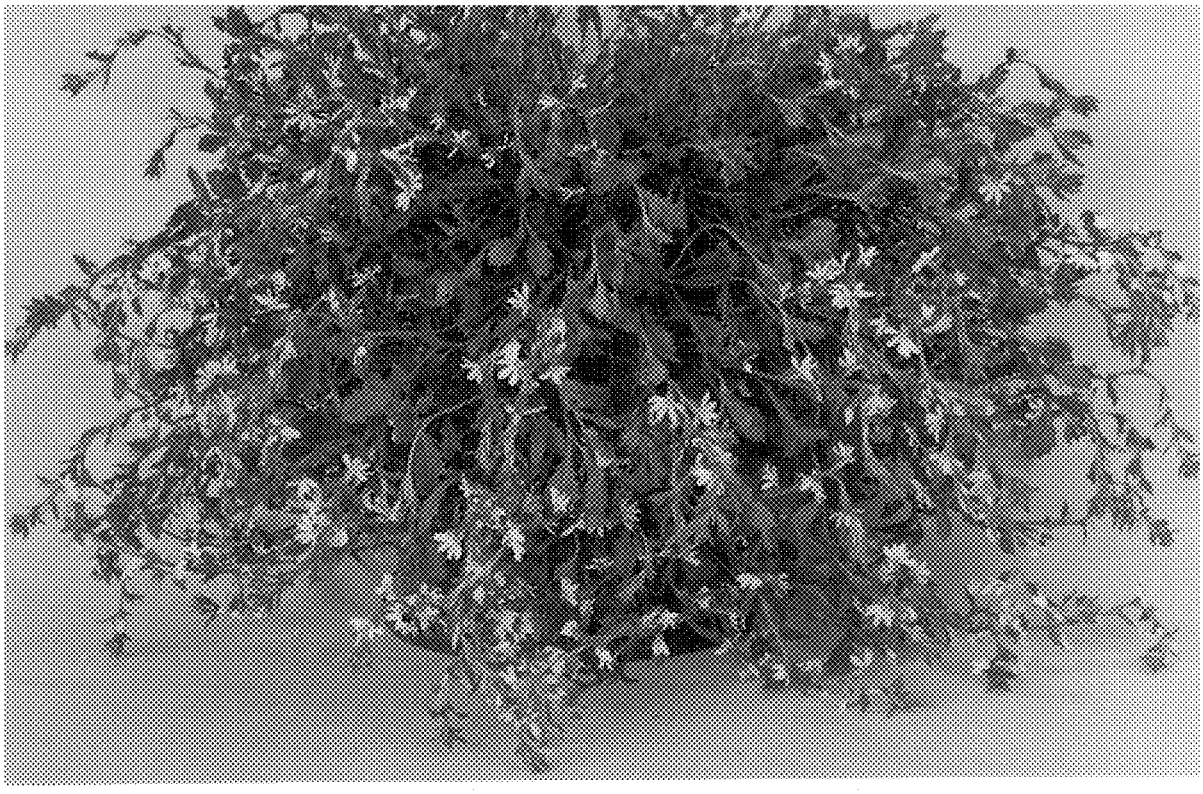
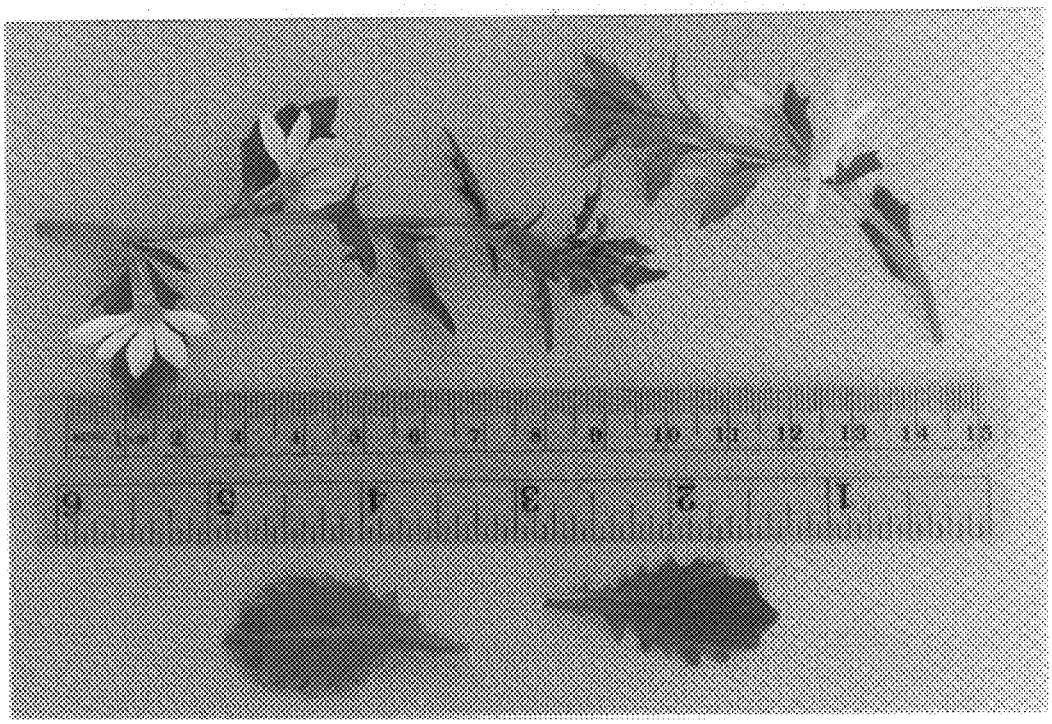

* * * * *